(12) United States Patent
Teles et al.

(10) Patent No.: US 7,026,493 B2
(45) Date of Patent: Apr. 11, 2006

(54) METHOD FOR PRODUCING AN EPOXIDE

(75) Inventors: Joaquim Henrique Teles, Otterstadt (DE); Alwin Rehfinger, Mutterstadt (DE); Anne Berg, Merksem (BE); Peter Rudolf, Ladenburg (DE); Norbert Rieber, Mannheim (DE); Peter Bassler, Viernheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 215 days.

(21) Appl. No.: 10/470,275

(22) PCT Filed: Feb. 6, 2002

(86) PCT No.: PCT/EP02/01218

§ 371 (c)(1),
(2), (4) Date: Aug. 7, 2003

(87) PCT Pub. No.: WO02/062779

PCT Pub. Date: Aug. 15, 2002

(65) Prior Publication Data

US 2004/0068128 A1  Apr. 8, 2004

(30) Foreign Application Priority Data

Feb. 7, 2001 (DE) ................. 101 05 527

(51) Int. Cl.
*C07D 301/12* (2006.01)
(52) U.S. Cl. ................. 549/531; 549/523; 549/529
(58) Field of Classification Search ................. 549/529, 549/531, 523
See application file for complete search history.

(56) References Cited

U.S. PATENT DOCUMENTS

| | | | |
|---|---|---|---|
| 3,947,501 A | | 3/1976 | Kollar |
| 4,833,260 A | * | 5/1989 | Neri et al. ................. 549/531 |
| 5,107,002 A | | 4/1992 | Shih |
| 5,288,882 A | | 2/1994 | Shih et al. |
| 5,863,391 A | | 1/1999 | Rueter et al. |
| 5,866,734 A | | 2/1999 | Flick et al. |
| 5,932,187 A | | 8/1999 | Ledon et al. |
| 6,024,840 A | | 2/2000 | Rueter |
| 6,183,638 B1 | | 2/2001 | Ledon et al. |
| 6,380,119 B1 | | 4/2002 | Grosch et al. |
| 6,479,680 B1 | | 11/2002 | Bassler et al. |
| 6,491,861 B1 | | 12/2002 | Grosch et al. |
| 6,518,441 B1 | | 2/2003 | Grosch et al. |
| 6,710,002 B1 | | 3/2004 | Grosch et al. |
| 6,727,371 B1 | | 4/2004 | Muller et al. |
| 2002/0082159 A1 | | 6/2002 | Grosch et al. |
| 2002/0120158 A1 | | 8/2002 | Grosch et al. |
| 2003/0050487 A1 | | 3/2003 | Muller et al. |
| 2003/0146080 A1 | | 8/2003 | Teles et al. |
| 2004/0152583 A1 | | 8/2004 | Grosch et al. |

FOREIGN PATENT DOCUMENTS

| | | |
|---|---|---|
| DE | 42 22 109 | 1/1994 |
| DE | 198 35 907 | 2/2000 |
| DE | 100 15 246 | 10/2001 |
| DE | 100 32 885 | 1/2002 |
| EP | 0311983 | 4/1989 |
| EP | 0 405 978 | 1/1991 |
| EP | 0 611 761 | 8/1994 |
| EP | 0 822 189 | 2/1998 |
| EP | 0 827 944 | 3/1998 |
| WO | WO 92/06918 | 4/1992 |
| WO | WO 98/54086 | 12/1998 |
| WO | WO 98/55228 | 12/1998 |
| WO | WO 98/55229 | 12/1998 |
| WO | WO 98/55430 | 12/1998 |

OTHER PUBLICATIONS

Waldemar Adam, et al., "The Mechanism of the Double Bond Cleavage in the Titanium Zeolite-Catalyzed Oxidation of α-Methylstyrene by Hydrogen Peroxide: The β-Hydroperoxy Alcohol as Intermediate", Chem. Ber., vol. 129, 1996, pp. 1453-1455.
Ullmann's Encyclopedia of Industrial Chemistry, 5$^{th}$ Edition, vol. 13, pp. 447-456, 1989.

* cited by examiner

Primary Examiner—Amelia A. Owens
(74) Attorney, Agent, or Firm—Oblon, Spivak, McClelland, Maier & Neustadt, P.C.

(57) ABSTRACT

An organic compound having at least one C—C double bond is epoxidized by means of hydrogen peroxide in the presence of at least one catalytically active compound and at least one solvent, wherein a product mixture comprising α-hydroperoxyalcohols is reduced using at least one reducing agent. The process advantageously comprises at least the following steps:
(i) reacting an organic compound having at least one C—C double bond with hydrogen peroxide in the presence of at least one catalytically active compound and at least one solvent to give a product mixture P1 comprising α-hydroperoxyalcohols;
(ii) separating an epoxide formed in the reaction in step (i) and the unreacted organic compound having at least one C—C double bond from P1 or P1' to give a product mixture P2 or P2', where P2 comprises the α-hydroperoxyalcohols formed as by-product in the reaction in step (i) and P2' is largely free of α-hydroperoxyalcohols;
(iii) treating P1 and/or P2 with at least one reducing agent so that the α-hydroperoxyalcohols are converted into corresponding glycols to give a product mixture P1' or P3.

8 Claims, No Drawings

METHOD FOR PRODUCING AN EPOXIDE

The present invention relates to a process for preparing an epoxide (epoxidation).

In the process of the present invention, the reaction mixture obtained in the reaction of an organic compound having at least one C—C double bond with hydrogen peroxide in the presence of at least one catalytic active compound and at least one solvent is worked up in such a way that the α-hydroperoxyalcohols formed as by-product of the epoxidation remain largely undecomposed or are converted into the corresponding glycols.

The term epoxides is used to refer to compounds which are formed by addition of oxygen onto the two carbon atoms of a double bond.

In the customary processes of the prior art, the compound to be epoxidized, generally a compound having at least one C—C double bond, is reacted with hydrogen peroxide in a solvent, for example methanol, and in the presence of a catalyst in an appropriate reactor. The general principles of this reaction are described in DE 198 35 907.1, 100 32 885.7 and 100 15 246.5.

The epoxide formed is separated off at the top together with the unreacted compound to be epoxidized, oxygen and other low-boiling by-products and a small proportion of solvent in the work-up by distillation. The distillation bottoms consist of a mixture comprising mainly solvent, water, unreacted hydrogen peroxide and high-boiling by-products. These can subsequently be reacted again with the compound to be epoxidized in an after-reactor. This gives a product stream composed mainly of solvent, water, epoxide and by-products.

To isolate the desired epoxide in pure form, the stream from the top of the distillation column and the output from the after-reactor are worked up further.

The most important by-products obtained in epoxidations are oxygen and products which can be formed by addition reactions of the solvent, of water or of hydrogen peroxide with the epoxide formed. Examples which may be mentioned are alkoxyalcohols, glycols and α-hydroperoxyalcohols.

If the solvent used is, for example, methanol and the compound to be epoxidized is propene, the most important by-products of the abovementioned type are 2-methoxy-1-propanol and 1-methoxy-2-propanol, propylene glycol, 2-hydroperoxy-1-propanol and 1-hydroperoxy-2-propanol.

While methoxypropanols and propylene glycol are very stable molecules, the hydroperoxypropanols are thermally labile molecules which tend to decompose to form further by-products, e.g. formaldehyde, acetaldehyde, propylene glycol and hydroxyacetone. Some of these by-products in turn tend to be converted into further, secondary by-products. Examples are formaldehyde dimethyl acetal, formic acid and methyl formate from formaldehyde or acetaldehyde dimethyl acetal, acetic acid and methyl acetate from acetaldehyde.

Some of these secondary by-products are those which cause particularly serious problems in the further work-up of the product mixture. For example, substances such as acetaldehyde and methyl formate can be separated by distillation from the mixture comprising the epoxide only with great difficulty.

Thus, U.S. Pat. No. 6,024,840 describes a complicated process for separating acetaldehyde from propylene oxide by means of a number of columns for extractive or fractional distillation connected in series.

Owing to the close proximity of the boiling points of methyl formate and propylene oxide, a high outlay in terms of apparatus is likewise necessary for separating them. Thus, U.S. Pat. No. 5,107,002 describes the removal of methyl formate with the aid of suitable basic ion exchange resins over which only the formate is reacted and thus removed.

The recovery and reprocessing of economically valuable substances from the product mixture and their reuse in the epoxidation has also hitherto been associated with the need for relatively complicated apparatus because of the presence of these by-products.

For example, preference is given to using methanol as solvent in epoxidation reactions. For economic reasons, efforts are made to recover this from the crude product mixture, to purify it and to return it to the reaction circuit. Problems are presented in this recycling procedure by, in particular, the presence of the by-products frequently present in the product mixture, e.g. acetaldehyde, acetaldehyde dimethyl acetal and methyl formate. It has hitherto been necessary to employ complicated apparatuses to achieve virtually complete removal of these interfering substances.

Thus, U.S. Pat. No. 5,863,391 states that a satisfactory result in the separation of aldehyde from methanol can only be achieved by extractive distillation carried out in a plurality of distillation columns connected in series. The process described in DE 10032885.7 for the separation of methyl formate from methanol is similarly complicated.

It is an object of the present invention to provide a process by means of which the formation of such by-products which are difficult to work up in epoxidation reactions is completely avoided or reduced to a minimum and the problems referred to above in the discussion of the prior art are thus also very largely avoided.

We have found that this object is achieved by a process for the epoxidation of an organic compound having at least one C—C double bond by means of hydrogen peroxide in the presence of at least one catalytically active compound and at least one solvent, wherein a product mixture comprising α-hydroperoxyalcohols is reduced using at least one reducing agent.

For the purposes of the present invention, organic compounds having at least one C—C double bond are all organic compounds which contain at least one C=C group.

In the process of the invention, preference is given to using organic compounds selected from the class of alkenes, which contain at least one such group.

In the process of the present invention, particular preference is given to using propene as alkene.

As examples of alkenes, mention may be made of the following: ethene, propene, 1-butene, 2-butene, isobutene, butadiene, pentenes, piperylene, hexenes, hexadienes, heptenes, octenes, diisobutene, trimethylpentene, nonenes, dodecene, tridecene, tetradecenes to eicosenes, tripropene and tetrapropene, polybutadienes, polyisobutenes, isoprenes, terpenes, geraniol, linalool, linalyl acetate, methylenecyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethol, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

In the process of the present invention, preference is given to using alkenes containing from 2 to 18 carbon atoms.

According to the present invention, the epoxidation of the abovementioned organic compounds having at least one C—C double bond is carried out using hydrogen peroxide.

To prepare the hydrogen peroxide used, it is possible to make recourse, for example, to the anthraquinone process by means of which virtually the entire world production of hydrogen peroxide is produced. This process is based on the catalytic hydrogenation of an anthraquinone compound to form the corresponding anthrahydroquinone compound, subsequent reaction of this with oxygen to form hydrogen peroxide and subsequent extraction of the hydrogen peroxide formed. The catalysis cycle is completed by rehydrogenation of the anthraquinone compound which has been formed again in the oxidation.

A review of the anthraquinone process is given in "Ullmanns Encyclopedia of Industrial Chemistry", 5$^{th}$ edition, volume 13, pages 447 to 456.

It is likewise conceivable to obtain hydrogen peroxide by anodic oxidation of sulfuric acid with simultaneous evolution of hydrogen at the cathode to produce peroxodisulfuric acid. Hydrolysis of the peroxodisulfuric acid forms firstly peroxosulfuric acid and then hydrogen peroxide and sulfuric acid, which is thus recovered.

It is of course also possible to prepare hydrogen peroxide from the elements.

Before use of hydrogen peroxide in the process of the present invention, it is possible to free, for example, a commercially available hydrogen peroxide solution of undesirable ions. Possible methods of carrying this out are, for example, those described in WO 98/54086, DE-A 42 22 109 or WO 92/06918. It is likewise possible for at least one salt present in the hydrogen peroxide solution to be removed from the hydrogen peroxide solution by means of ion exchange in an apparatus which comprises at least one nonacidic ion exchange bed having a cross-sectional area through which flow occurs F and a height H such that the height H of the ion exchange bed is less than or equal to $2.5 \cdot F^{1/2}$, in particular less than or equal to $1.5 \cdot F^{1/2}$. For the purposes of the present invention, all nonacidic ion exchange beds comprising cation exchangers and/or anion exchangers can in principle be used. It is also possible for cation and anion exchangers to be used as mixed beds within one ion exchange bed. In a preferred embodiment of the present invention, only one type of nonacidic ion exchangers is used. Further preference is given to the use of a basic ion exchanger, particularly preferably a basic anion exchanger and very particularly preferably a weakly basic anion exchanger.

The reaction according to the present invention of the organic compounds having at least one C—C double bond with hydrogen peroxide takes place in the presence of at least one catalytically active compound.

In general, all catalysts known to those skilled in the art are suitable for the purposes of the present invention. However, preference is given to using zeolite catalysts.

Accordingly, the present invention also provides a process of the abovementioned type in which the catalytically active compound or compounds comprises a zeolite catalyst.

The zeolite catalysts which can be used in the process of the present invention are subject to no particular restrictions.

Zeolites are, as is known, crystalline aluminosilicates having ordered channel and cage structures and containing micropores which are preferably smaller than about 0.9 nm. The network of such zeolites is built up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolite Structure Types", Elsevier, 4$^{th}$ Edition, London 1996.

Zeolites which contain no aluminum and in which the Si(IV) in the silicate lattice is partly replaced by titanium as Ti(IV) are also known. These titanium zeolites, in particular those having a crystal structure of MFI type, and possible ways of preparing them are described, for example, in EP-A 0 311 983 or EP-A 405 978. Apart from silicon and titanium, such materials may further comprise additional elements such as aluminum, zirconium, tin, iron, cobalt, nickel, gallium, boron or small amounts of fluorine. In the preferably regenerated zeolite catalysts used in the process of the present invention, the titanium of the zeolite can be partly or wholly replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Titanium zeolites, in particular those having a crystal structure of the MFI type, and possible ways of preparing them are described, for example, in WO 98/55228, WO 98/03394, WO 98/55229, WO 98/55430, EP-A 0 311 983 or EP-A 0 405 978, whose relevant contents are fully incorporated by reference into the present application.

It is known that titanium zeolites having an MFI structure can be identified by means of a particular X-ray diffraction pattern and also by means of a lattice vibration band in the infrared (IR) at about 960 cm$^{-1}$ and can in this way be distinguished from alkali metal titanates or crystalline and amorphous $TiO_2$ phases.

Specific mention may be made of titanium-, germanium-, tellurium-, vanadium-, chromium-, niobium- and zirconium-containing zeolites having a pentasil zeolite structure, in particular the types assigned X-ray-crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structures and also mixed structures comprising two or more of the abovementioned structures. Furthermore, titanium-containing zeolites having the ITQ-4, SSZ-24, TTM-1, UTD-1, CIT-1 or CIT-5 structure can also be used in the process of the present invention. Further titanium-containing zeolites which may be mentioned are those having the ZSM-48 or ZSM-12 structure.

For the purposes of the present invention, preference is given to using Ti zeolites having an MFI structure, MEL structure or MFI/MEL mixed structures. Further specific examples of preferred catalysts are the Ti-containing zeolite catalysts which are generally referred to as "TS-1", "TS-2", "TS-3", and also Ti zeolites having a lattice structure isomorphous with β-zeolite.

Accordingly, the present invention also provides a process as described above in which the catalyst is a titanium silicalite having the TS-1 structure.

Solvents suitable for use in the epoxidation are in principle all solvents which are known for this purpose to a person skilled in the art. Preference is given to using organic solvents such as alcohols, either individually or as a mixture of two or more thereof. Alcohol/water mixtures can also be used. In the process of the present invention, preference is given to using methanol as solvent in the epoxidation.

The amounts of solvent used can be varied within wide limits. Possible amounts of solvent used for the purposes of the present invention are from 5 to 25 g of methanol per gram of hydrogen peroxide used. The solvent is preferably used in an amount of from 8 to 16 g of methanol per gram of hydrogen peroxide used, particularly preferably from 10 to 14 g of methanol per gram of hydrogen peroxide used.

The epoxidation reaction under discussion forms a product mixture which includes, inter alia, α-hydroperoxyalcohols. This product mixture is reduced. In this reduction, the α-hydroperoxyalcohols are reduced selectively to the corresponding glycols (1,2-diols) so as to prevent the formation, by nonspecific decomposition, of the above-described primary or secondary by-products which cause the problems mentioned above in the further work-up of the product mixture. The further work-up of the product mixture can thus be carried out in a largely trouble-free manner using apparatus of reduced complexity compared to the prior art.

The reduction can be carried out using all reducing agents described for this purpose in the literature. However, preference is given to those which can be employed in an aqueous methanolic solution. The reducing agents can be used individually or as mixtures of two or more thereof.

Some reducing agents and reduction methods suitable for the present purposes are described by way of example below. All reduction conditions known to those skilled in the art for the respective reduction using the reducing agent chosen in each case can be employed. The reduction process chosen can be carried out continuously or batchwise.

Thus, for example, the respective α-hydroperoxyalcohol-containing product mixture can be reduced using phosphorus(III) compounds such as $PCl_3$, phosphines (e.g. triphenylphosphine, tributylphosphine), phosphorous acid or its salts or sodium hypophosphite ($NaH_2PO_2$).

Reduction using sulfur(II) compounds, for example $H_2S$ or its salts, sodium polysulfides ($Na_2S_x$, x>1), dimethyl sulfide, tetrahydrothiophene, bis(hydroxyethyl) sulfide or sodium thiosulfate ($Na_2S_2O_3$), or using sulfur(IV) compounds, for example sulfurous acid ($H_2SO_3$) and its salts, sodium bisulfite ($Na_2S_2O_5$) or thiourea S-oxide, also leads to the desired result, viz. reduction of α-hydroperoxyalcohols to the corresponding glycols.

Furthermore, α-hydroperoxyalcohols can also be reduced to the corresponding glycols by reaction of the product mixture in which they are present with nitrites, for example sodium nitrite or isoamyl nitrite, or by reaction with α-hydroxycarbonyl compounds, for example hydroxyacetone, dihydroxyacetone, 2-hydroxycyclopentanone (glutaroin), 2-hydroxycyclohexanone (adipoin), glucose and other reducible sugars.

Further possible reducing agents are enediols, for example ascorbic acid, or compounds which contain a B—H bond, for example sodium borohydride or sodium cyanoborohydride.

In the process of the present invention, preference is given to reducing α-hydroperoxyalcohol-containing product mixtures by catalytic hydrogenation.

Accordingly, the present invention also provides a process for the epoxidation of the abovementioned type, in which the reducing agent or agents comprises at least one compound which is suitable for catalytic hydrogenation.

An example of such a suitable compound is hydrogen in the presence of a suitable hydrogenation catalyst.

For the purposes of the present invention, catalytic hydrogenation is thus the reaction of an α-hydroperoxyalcohol-containing product mixture with hydrogen in the presence of a suitable hydrogenation catalyst.

The hydrogenation catalyst in question can be either homogeneous or heterogeneous. For the purposes of the present invention, the catalytic hydrogenation is preferably carried out in the presence of a heterogeneous catalyst.

The hydrogenation catalyst comprises at least one active metal of group VIIb, VIII, Ia or Ib of the Periodic Table of the Elements, either individually or as a mixture of two or more thereof.

In the process of the present invention, use is made of palladium (Pd), platinum (Pt), rhodium (Rh), ruthenium (Ru), iridium (Ir), osmium (Os), iron (Fe), cobalt (Co), nickel (Ni) and copper (Cu), preferably Pd, Pt, Rh, Ru and Ir, particularly preferably Pd.

These can also be used in powder form. The active metal powder can be prepared by various methods. Customary methods are, for example, thermal decomposition of active metal salts, the reduction of aqueous or nonaqueous active metal salt solutions using, for example, hydrazine, formaldehyde, hydrogen or other reducing agents. Active metal powders can comprise one active metal or a mixture of two or more thereof.

Active metal bodies can also be used for the hydrogenation. In this case, foils, wires, meshes (which can be prepared by weaving and knitting), granules and crystallite powders produced from one active metal or a mixture of two or more thereof are preferably employed.

Furthermore, it is also possible to use active metal oxides, for example as suspensions comprising one active metal or a mixture of two or more thereof, for the catalytic hydrogenation.

In the process of the present invention, preference is given to using hydrogenation catalysts which comprise a composite of an active metal or a mixture of two or more thereof and at least one support material.

The active metal content is, if the active metal is selected from the group consisting of Pd, Pt, Rh, Ir, Ru and Os, generally in a range from 0.01 to 10% by weight. If an active metal selected from the group consisting of Fe, Co, Ni and Cu is present, the content is generally in a range from 1 to 80% by weight.

Support materials which can be used are all materials which are known for this purpose to those skilled in the art and have sufficient chemical and thermal stability for the respective use. Examples are porous oxides such as aluminum oxide, silicon dioxide, aluminosilicates, zeolites, titanium oxide, zirconium oxide, chromium oxide, zinc oxide, magnesium oxide, rare earth oxides, and also activated carbon or mixtures of two or more of the compounds mentioned. Furthermore, all types of support materials described in EP 0 827 944 A1 can also be used.

The composites which can be produced from an active metal or a mixture of two or more thereof and at least one support, known as supported catalysts, can be produced by any method known to those skilled in the art.

For example, such supported catalysts are generally obtainable by impregnating the support or supports with a solution of the active metal or mixture of two or more thereof; in the case of a plurality of active metals, these can be added simultaneously or in succession. It is possible to impregnate the support fully or only partly with such a solution.

Of course, it is also possible to spray the respective solution of appropriate active metals onto the support by methods known per se or to apply the active metals to the support by vapor deposition or by electrochemical deposition. The application of the active metal or a mixture of two or more thereof can also be carried out in the manner described in EP 0 827 944 A1.

In both methods, the desired alkali metal loading of the support is set via the concentration of the active metal solution selected in each case.

In the catalyst precursors produced in this way, the active metal or mixture of two or more thereof can be uniformly distributed over the radius or can be present in higher concentration in a shell. In the present case, a shell is an outer radial region of the catalyst precursor (support) in which the active metal is present in a higher concentration than in the other regions of the catalyst precursor (support).

Impregnation or spraying can generally be followed by further steps such as a drying step and/or a heat treatment and also a calcination step.

Supported catalysts can generally also be obtained by precipitating at least one precursor of the active metal in the presence of at least one suitable support material by means of alkali or a reducing agent. The catalyst precursors obtained in this way can then be brought into a shape suitable for the respective application, for example extrudates or pressed pellets. This can generally also be followed by the abovementioned further steps such as drying, heat treatment and calcination.

As precursors of the active metals, it is in principle possible to use all water-soluble active metal compounds, for example readily water-soluble salts or complexes of the active metals, e.g. nitrates, nitrosyl nitrates, chlorides, acetates, formates and sulfates and also chlorometalates.

Drying of the catalyst precursors can be carried out by all drying methods known to those skilled in the art. For the purposes of the present invention, the drying process is preferably carried out at from 80 to 150° C., particularly preferably from 80 to 120° C.

The calcination of the catalyst precursors can be carried out in any way known to those skilled in the art. For the purposes of the present invention, the catalyst precursors obtained are preferably exposed to a gas stream comprising air or nitrogen at from 150 to 500° C., particularly preferably from 200 to 450° C.

In general, the calcination process can be followed by the activation of the catalyst precursors obtained in this way.

Activation can be carried out by all methods known for this purpose to those skilled in the art in which the catalyst precursors are exposed to a reducing atmosphere, for example a hydrogen-containing atmosphere at room temperature or elevated temperature.

For the purposes of the present invention, catalyst precursors comprising an active metal selected from the group consisting of Pd, Pt, Rh, Ir, Ru and Os can be treated with hydrogen at from 80 to 250° C., preferably from 80 to 180° C. Catalyst precursors comprising an active metal selected from the group consisting of Fe, Co, Ni and Cu are preferably treated with hydrogen at from 150 to 500° C., particularly preferably from 200 to 450° C.

The duration of the treatment with hydrogen at room temperature or elevated temperatures depends on the concentration of the active metal or mixture of two or more thereof.

For the purposes of the present invention, the duration of the treatment is preferably from 0.5 to 24 hours, particularly preferably from 1 to 5 hours, in the case of catalyst precursors comprising an active metal selected from the group consisting of Pd, Pt, Rh, Ir, Ru and Os. In the case of catalyst precursors comprising an active metal selected from the group consisting of Fe, Co, Ni and Cu, the duration of the treatment is preferably from 12 to 120 hours, particularly preferably from 24 to 72 hours.

The space velocity of hydrogen in the activation carried out for the purposes of the present invention is generally from 1 to 100 $l\,kg^{-1}_{catalyst}\,h^{-1}$, but preferably from 10 to 50 $l\,kg^{-1}_{catalyst}h^{-1}$.

The hydrogenation catalysts prepared in the above-described way make it possible to carry out hydrogenations by any method known to those skilled in the art, for example in the liquid phase, in a fixed bed or in suspension and in the upflow mode or downflow mode. However, the hydrogenation in the process of the present invention is preferably carried out in a fixed bed.

Pressure and temperature ranges in the hydrogenation are chosen as a function of the substance or mixture to be hydrogenated. In the process of the present invention, the hydrogenation is preferably carried out in a pressure range from 1 to 100 $bar_{abs}$, particularly preferably from 1 to 10 $bar_{abs}$, and preferably at temperatures in the range from 0 to 180° C., more preferably from 25 to 120° C., in particular from 40 to 80° C.

In a hydrogenation carried out in a fixed bed, the residence time of the liquid is from 1 second (s) to 1 hour (h), preferably from 10 s to 20 minutes (min), in particular from 30 s to 5 min.

Accordingly, the catalyst used in the catalytic hydrogenation of an α-hydroperoxyalcohol-containing product mixture formed in the epoxidation according to the present invention is selected from the group consisting of heterogeneous catalysts comprising Ru, Ni, Pd, Pt, either individually or as a mixture of two or more thereof, as active metal on a suitable support material.

Preference is given to using supported catalysts which are produced by one of the above-described methods and are used for the hydrogenation of the α-hydroperoxyalcohol-containing product mixture.

The hydrogenation of the α-hydroperoxyalcohol-containing product mixture can be carried out within the various process steps of the epoxidation according to the present invention.

The present invention therefore also provides a process for the epoxidation of an organic compound having at least one C—C double bond by means of hydrogen peroxide in the presence of at least one catalytically active compound and at least one solvent, which comprises at least the following steps:

(i) reacting an organic compound having at least one C—C double bond with hydrogen peroxide in the presence of at least one catalytically active compound and at least one solvent to give a product mixture P1 comprising α-hydroperoxyalcohols;

(ii) separating an epoxide formed in the reaction in step (i) and the unreacted organic compound having at least one C—C double bond from P1 or P1' to give a product mixture P2 or P2', where P2 comprises the α-hydroperoxyalcohols formed as by-product in the reaction in step (i) and P2' is largely free of α-hydroperoxyalcohols;

(iii) treating P1 and/or P2 with at least one reducing agent so that the α-hydroperoxyalcohols are converted into corresponding glycols to give a product mixture P1' or P3.

The reaction in step (i) can be carried out in a reactor, preferably an approximately isothermal shell-and-tube reactor, in which the reaction is carried out under superatmospheric pressure without a gas phase being present.

The product mixture P1 formed generally comprises the by-product α-hydroperoxyalcohol, the solvent used, water, the desired epoxide, proportions of unreacted organic compound having at least one C—C double bond together with further by-products, for example oxygen and products which are formed by an addition reaction of the solvent or of water with the epoxide.

After this process step (i) it is possible to reduce the α-hydroperoxyalcohol-containing product mixture P1 in the above-described manner by carrying out a step (iii) in which the α-hydroperoxyalcohols are converted into the corresponding glycols to give a further product mixture P1'.

However, this step can also be omitted.

If step (iii) is carried out directly after step (i), the product mixture P1' used in step (ii) is largely free of α-hydroperoxyalcohols.

If the step (iii) does not directly follow the step (i), then P1 still contains α-hydroperoxyalcohols.

In step (ii), the desired epoxide and the unreacted organic compound having at least one C—C double bond can be separated off from the product mixture P1 or P1'. This separation in step (ii) gives a product mixture P2 or P2'.

The separation can be carried out by any method known to those skilled in the art for this purpose, for example by distillation, appropriate precipitation reactions, extraction and also membrane permeation.

For the purposes of the present invention, the separation is preferably carried out by distillation.

Accordingly, the present invention further provides a process according to the present invention in which the epoxide formed in step (i) and the unreacted organic compound having at least one C—C double bond are separated off in step (ii) by distillation.

The separation by distillation can be carried out using a distillation apparatus known to those skilled in the art for this purpose. It can be carried out either continuously or batchwise.

The distillation of α-hydroperoxyalcohol-free product mixtures such as P1' does not have to be carried out under any particular conditions. It can be carried out under the general distillation conditions in respect of pressure, temperature and residence time in the liquid phase with which a person skilled in the art is familiar.

However, if still α-hydroperoxyalcohol-containing product mixtures such as P1 are distilled, then certain conditions are necessary. The distillation is carried out in such a way that it can be ensured that α-hydroperoxyalcohols remain largely, i.e. to an extent of preferably >80%, particularly preferably >90%, undecomposed or preferably completely undecomposed.

The present invention therefore also provides a process according to the present invention in which the epoxide formed in step (i) and the unreacted organic compound having at least one C—C double bond are distilled off in step (ii) at below 80° C., measured at the bottom of the apparatus used for the distillation, and at a residence time of less than 4 hours in the bottom of this apparatus.

The residence time in the bottom of the distillation apparatus is preferably less than 2 hours, particularly preferably less than 1 hour, and the temperature at the bottom of the distillation apparatus is preferably below 75° C., particularly preferably below 70° C.

In general, the distillation is carried out at a temperature which is established on distillation under atmospheric pressure.

The distillation is particularly preferably carried out at a temperature of 65±2° C. at the bottom of the distillation apparatus and a residence time of about 2 hours.

Apart from the desired epoxide and the unreacted organic compound having at least one C—C double bond, oxygen which may be present in P1 or P1', other low-boiling by-products and a small proportion of solvent are also taken off at the top of a distillation column. The bottom product from this column is the product mixture P2. P2 consists mainly of solvent, water, unreacted hydrogen peroxide and high-boiling and other by-products. α-Hydroperoxyalcohols are also present in P2.

The α-hydroperoxyalcohol-containing product mixture P2 can be reduced by means of the reaction described in step (iii) to give a further product mixture P3, with the α-hydroperoxyalcohols being converted into the corresponding glycols in this reaction.

For economic reasons, it is desirable to recover the solvent from the crude product mixture, purify it and return it to the process. To avoid the problems described at the outset which occur when the solvent is recovered in the presence of α-hydroperoxyalcohols, the solvent is generally recovered from the product mixture which has already been reduced, i.e. which is largely free of α-hydroperoxyalcohols.

The product mixture P2 still contains α-hydroperoxyalcohols. For this reason, it is advantageous for it firstly to be reduced as described above to give the product mixture P3 so that the solvent can subsequently be separated off from P3, purified and returned to the process.

The product mixture P2' is already free of α-hydroperoxyalcohols. The solvent can therefore be separated off from it directly and be worked up for reuse.

The present invention therefore also provides a process according to the present invention in which the solvent present in the respective product mixture after step (iii) is wholly or partly separated off and, if desired, recirculated to step (i). The solvent is preferably recirculated.

In the reduction of α-hydroperoxyalcohol-containing product mixtures, it is also advantageous for not only the α-hydroperoxyalcohols to be reduced but also any residual hydrogen peroxide present in the product mixture to be reduced to water. This reduces the danger which could be posed by uncontrolled decomposition of hydrogen peroxide to form oxygen.

This is particularly advantageous when the reduction of step (iii) is carried out only after the separation of step (ii).

Both economic and environmental considerations make it desirable for by-products formed in the epoxidation process to be utilized in a purposeful manner. In the present novel process, the glycols (1,2-diols) formed by reduction of the α-hydroperoxyalcohol-containing product mixture can be separated off as further useful products and be passed to other processes, for example as starting materials or solvents.

Accordingly, the present invention also provides a process according to the present invention in which the glycols obtained in a reduction of an α-hydroperoxyalcohol-containing product mixture can be separated off as further useful products.

The glycols can be separated off by any method known for this purpose to those skilled in the art, for example distillation, extraction or membrane permeation.

The glycols which have been separated off have a variety of uses. For example, they can be used as starting materials for syntheses in the plastics industry or for the synthesis of naturally occurring compounds and also generally as solvents in large areas of industry.

The present invention therefore also provides for the use of the glycols separated off as further useful products in the process of the present invention for further applications in all fields known to those skilled in the art.

The process of the present invention is preferably used for the epoxidation of propene to propene oxide by means of hydrogen peroxide in methanolic solution in the presence of a titanium silicalite having an MFI structure. This embodiment of the process of the present invention is described in detail below.

The α-hydroperoxyalcohols formed as by-products in this reaction are 1-hydroperoxy-2-propanol and 2-hydroperoxy-1-propanol. They can be reduced by means of the reduction according to the present invention to propylene glycol (1,2-propanediol) which can be separated off as a further useful product.

Propylene glycol has a variety of uses, for example as antifreeze, as brake fluid, for producing alkyl and polyester resins, as plasticizer for vinyl polymers, as solvent for fats, oils, resins, waxes, dyes, etc. In the food industry, propylene glycol is also used, for example, as solvent for dyes and flavors. It is also employed as humectant for tobacco products and in cosmetics, and also as carrier in various ointments, creams and pharmaceuticals. If the optically active form is separated off, it can be used as chiral building block in various organic syntheses.

Propylene glycol is also, quite generally, a compound which is very frequently used as starting material in the synthesis of further auxiliaries or basic chemicals for the chemical industry. Thus, after esterification or etherification of one or both hydroxyl groups, it is frequently used as solvent, as plasticizer or thickener and also as emulsifier. The polyaddition of propylene glycol also leads to further important polymers which can be used in industrial processes.

In a preferred embodiment of the process of the present invention for the epoxidation of propene to propene oxide, propene is reacted with hydrogen peroxide in methanol over a TS-1 catalyst in the form of extrudates in a main reactor (approximately isothermal shell- and-tube reactor under superatmospheric pressure, without gas phase) (step (i); leads to a product mixture P1). In this reaction, from 75 to 95% of the hydrogen peroxide are reacted.

Downstream of the main reactor, the resulting propylene oxide together with unreacted propene, oxygen and further low-boiling by-products and a small proportion of methanol are separated off at the top of a distillation column (step (ii); leads to a product mixture P2, the distillation bottoms).

The bottoms from this column (P2) consists mainly of methanol, water and the unreacted hydrogen peroxide together with high-boiling by-products. This product mixture is transferred to at least one further reactor, known as an after-reactor. The after-reactor is preferably an approximately adiabatic tube reactor operated under superatmospheric pressure and without a gas phase being present.

There, the bottoms (P2) are reacted with propene again (corresponds to a step (i) being carried out again).

This step produces a further product mixture (P1) which consists mainly of methanol, water, propylene oxide and by-products, including the α-hydroperoxyalcohols such as 1-hydroperoxy-2-propanol and 2-hydroperoxy-1-propanol. In addition, this product mixture generally contains less than 0.1% by weight of unreacted hydrogen peroxide.

After the reaction in the after-reactor, the resulting product mixture is worked up further to isolate the propylene oxide and, if desired, the propylene glycol.

One possibility is firstly to reduce the product mixture (step (iii)) to convert the by-products which cause problems (α-hydroperoxyalcohols) into propylene glycol. Propylene oxide and unreacted propene can subsequently be separated off by distillation (step (ii)) for further work-up. This is followed by recovery of the solvent methanol and separation of the further useful product propylene glycol from the remaining distillation bottoms.

Another possibility is firstly to remove propylene oxide and unreacted propene from the product mixture from the after-reactor by distillation under the conditions indicated above for distillation of α-hydroperoxyalcohol-containing product mixtures (step (ii)), then to reduce the distillation bottoms (step (iii)) and to separate both the propylene glycol formed in this way and the solvent methanol from the reduced bottoms.

It is also possible to combine the product mixtures which are obtained after carrying out step (iii) and which are largely free of α-hydroperoxyalcohols. Propylene glycol and methanol can then likewise be separated off from this combined product mixture.

Of course, each of the steps to be carried out can be formed a plurality of times in succession, with the product mixture formed in each case being collected and the combined product mixtures then being passed to the subsequent step.

If more than 0.1% by weight of hydrogen peroxide is found in the output from the after-reactor, it is of course possible for the bottoms obtained in the distillation (step (ii)) to be reacted once more with propene in a further after-reactor in the above-described sequence of steps, thus forming a reactor cascade.

For the purposes of the present invention, preference is given to the following reaction sequence (A):
1. an organic compound having at least one C—C double bond is reacted with hydrogen peroxide in the presence of at least one catalytically active compound and at least one solvent in a step (i) to form a product mixture P1 (α-hydroperoxyalcohol-containing);
2. the product mixture P1 is treated with at least one reducing agent in a step (iii) to convert the α-hydroperoxyalcohols into the corresponding glycols to give a further product mixture P1' (α-hydroperoxyalcohol-free);
3. an epoxide formed in the reaction in 1. (step (i)) and the unreacted organic compound having at least one C—C double bond is separated off from P1' in step (ii), giving a product mixture P2';
4. the glycols corresponding to the α-hydroperoxyalcohols and also the solvent can now be separated off from P2' in the manner described above.

However, particular preference is given to the following reaction sequence (B):
1. an organic compound having at least one C—C double bond is reacted with hydrogen peroxide in the presence of at least one catalytically active compound and at least one solvent in a step (i) to form a product mixture P1 (α-hydroperoxyalcohol-containing);
2. an epoxide formed in the reaction in 1. (step (i)) and the unreacted organic compound having at least one C—C double bond are separated off from P1 in step (ii), giving a product mixture P2;
3. the product mixture P2 is treated with at least one reducing agent in a step (iii) to convert the α-hydroperoxyalcohols into the corresponding glycols to give a further product mixture P3 (α-hydroperoxyalcohol-free);
4. the glycols corresponding to the α-hydroperoxyalcohols and also the solvent can now be separated off from P3 in the manner described above.

The invention is illustrated by the examples below.

EXAMPLE (B1)

Reaction of propene with hydrogen peroxide

A tube reactor (length: 2 m, diameter: 45 mm) provided with cooling jacket and pressure regulator was charged with 620 g of a TS-1 catalyst in the form of extrudates (produced as described in WO 98/55229).

A mixture of methanol (1560 g/h), aqueous hydrogen peroxide solution (330 g/h, about 40% by weight in water) and propylene (245 g/h) was passed through this reactor at a pressure of 20 bar.

The temperature of the cooling medium in the reactor jacket was set (depending on the catalyst activity, to from 20 to 50° C.) so that approximately 90% of the hydrogen peroxide had been reacted in the output from the reactor. The conversion was determined by measuring the concentration of hydrogen peroxide in the output using the titanyl sulfate method.

The output from the reactor was depressurized and worked up in a continuous distillation column at atmospheric pressure. The distillation conditions were selected so that virtually the total amount of unreacted propylene and propylene oxide formed was distilled off via the top. A certain proportion of the methanol goes over at the top (approximately the same amount as propylene oxide). The temperature at the bottom of the column was about 67° C. and the residence time at the bottom was about 1 hour.

The bottom product obtained was a mixture having the following average composition (in % by weight):
methanol (81), water (17), hydrogen peroxide (0.9), hydroperoxypropanols (sum of the two isomers, 0.4), 1-methoxy-2-propanol (0.3), 2-methoxy-1-propanol (0.2), propylene glycol (0.1).

COMPARATIVE EXAMPLE (CI)

The output from the reactor in B1 was fed without further treatment into a second continuous distillation column operated at atmospheric pressure.

In this column, the mixture was separated into a largely water-free methanol fraction (top product) and a largely methanol-free water fraction (bottom product). The temperature at the bottom was about 99° C. and the residence time at the bottom was about 1 hour.

Owing to the higher temperature in this column, both hydrogen peroxide and the α-hydroperoxypropanols were decomposed.

The methanol fraction obtained at the top contained the following impurities (% by weight):
acetaldehyde (0.1), 1,1-dimethoxyethane (0.2), methyl formate (0.002).

In addition, the incondensable offgas at the top of the column contained considerable amounts of oxygen and has to be made inert by means of nitrogen. This methanol stream can therefore not be reused for the propylene epoxidation without further treatment.

Neither acetaldehyde nor 1,1-dimethoxyethane nor methyl formate were reacted in the epoxidation reactors. Acetaldehyde and 1,1-dimethoxyethane would thus accumulate in the methanol stream as time goes on. On the other hand, the methyl formate would not accumulate but would, (owing to the very similar boiling points) appear in the propylene oxide as an impurity which is difficult to remove.

The water fraction at the bottom of the column contained the following impurities (% by weight):
1-methoxy-2-propanol (1.5), 2-methoxy-1-propanol (1.3), propylene glycol (0.9), formic acid (0.5), formaldehyde (0.2) and hydroxyacetone (0.2). Although propylene glycol is regarded as a potential useful product, the concentration is too low for it to be recovered economically from this stream.

EXAMPLE (E2)

The mixture from E1 was collected and about 5 kg thereof were hydrogenated at 50° C. and 10 bar of hydrogen in an autoclave until no more hydrogen was taken up (about 1 hour). The hydrogenation catalyst used was a supported catalyst comprising 5% by weight of Pd on activated carbon (10 g).

The crude product from the hydrogenation contained no peroxides and was, after removal of the catalyst by filtration, separated in a batchwise distillation at atmospheric pressure into a largely water-free methanol fraction (top product) and a largely methanol-free water fraction (bottom product). The temperature at the bottom was about 99° C. at the end of the distillation and the distillation time was about 8 hours.

The methanol fraction from the top contained no detectable impurities other than water (about 100 ppm). This methanol stream could thus be recirculated without further treatment to the process for the epoxidation of propylene.

The water fraction remaining at the bottom contained only the following impurities (% by weight):
1-methoxy-2-propanol (1.5), 2-methoxy-1-propanol (1.2), propylene glycol (2.5) and dipropylene glycol monomethyl ether (mixture of isomers, in traces).

Neither formic acid nor formaldehyde nor hydroxyacetone were able to be detected.

Due to the significantly higher concentration of propylene glycol in the water fraction, this can be isolated as useful product and can be utilized further in an economical fashion.

The examples thus show that the process of the present invention avoids the disadvantages which occur in the prior art due to the α-hydroperoxyalcohols formed as by-products. It thus represents a highly valuable industrial process for the epoxidation of compounds having at least one C—C double bond, in which, as a result of the way in which the process is carried out according to the invention, the epoxide can be separated off in pure form, further useful products (viz. the glycols corresponding to the α-hydroperoxyalcohols) can be obtained and the solvent used can simultaneously be recovered in a simple fashion using apparatus which is less complicated than in the case of the prior art.

We claim:

1. A process for the epoxidation of an organic compound having at least one C—C double bond by reacting the organic compound with hydrogen peroxide in the presence of at least one catalytically active compound and at least one solvent, wherein a product mixture comprising α-hydroperoxyalcohols is reduced using at least one reducing agent, which comprises at least the following steps:

(i) reacting an organic compound having at least one C—C double bond with hydrogen peroxide in the presence of at least one catalytically active compound and at least one solvent to give a product mixture P1 comprising α-hydroperoxyalcohols;

(ii) separating an epoxide formed in the reaction in step (i) and the unreacted organic compound having at least one C—C double bond from P1 to give a product mixture P2, where P2 comprises the α-hydroperoxyalcohols formed as by-product in the reaction in step (i);

(iii) treating P2 with at least one reducing agent so that the α-hydroperoxyalcohols are converted into corresponding glycols to give a product mixture P3.

2. A process as claimed in claim 1, wherein the solvent present in the respective product mixture P3 after step (iii) is wholly or partly separated off and, optionally, recirculated to step (i).

3. A process as claimed in claim 1, wherein the reducing agent or agents comprise(s) at least one compound which is suitable for catalytic hydrogenation.

4. A process as claimed in claim 3, wherein the catalyst which is suitable for catalytic hydrogenation is a heterogeneous catalyst comprising Ru, Ni, Pd, or Pt, either individually or as a mixture of two or more thereof, as active metal on a suitable support material.

5. A process as claimed in claim 1, wherein the epoxide formed in step (i) and the unreacted organic compound having at least one C—C double bond are separated off in step (ii) by distillation.

6. A process as claimed in claim 5, wherein the separation by distillation is carried out at below 80° C., measured at the bottom of the distillation apparatus, and at a residence time of less than 4 hours in the bottom of the distillation apparatus.

7. A process as claimed in claim 1, wherein the glycols formed in a reduction of an α-hydroperoxyalcohol-containing product mixture are separated off as further useful products.

8. A process as claimed in claim 1, wherein propene is epoxidized to propene oxide by means of hydrogen peroxide in methanolic solution in the presence of a titanium silicalite having an MFI structure.

* * * * *